US011345102B2

(12) United States Patent
Terada et al.

(10) Patent No.: US 11,345,102 B2
(45) Date of Patent: May 31, 2022

(54) TORIC LENS, OPTICAL ELEMENT, AND IMAGE FORMING APPARATUS

(71) Applicant: CANON KABUSHIKI KAISHA, Tokyo (JP)

(72) Inventors: Junji Terada, Tokyo (JP); Toshiaki Yoshikawa, Yokohama (JP); Kazuhiro Arai, Yokohama (JP); Noriyuki Nakai, Machida (JP); Yu Kameno, London (GB); Miwa Takachi, Kawasaki (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 225 days.

(21) Appl. No.: 16/653,677

(22) Filed: Oct. 15, 2019

(65) Prior Publication Data
US 2020/0114601 A1   Apr. 16, 2020

(30) Foreign Application Priority Data
Oct. 16, 2018   (JP) .............................. JP2018-195286

(51) Int. Cl.
B29D 11/00   (2006.01)
G03G 15/00   (2006.01)
G03G 15/043  (2006.01)
A61F 2/16    (2006.01)
G02C 7/06    (2006.01)

(52) U.S. Cl.
CPC .. B29D 11/00019 (2013.01); B29D 11/00509 (2013.01); G03G 15/043 (2013.01); A61F 2/1645 (2015.04); G02C 7/06 (2013.01)

(58) Field of Classification Search
CPC ... A61F 2/1645; G02C 7/06; B29D 11/00019; B29D 11/00509
See application file for complete search history.

(56) References Cited

U.S. PATENT DOCUMENTS

| | | | |
|---|---|---|---|
| 10,723,877 B2* | 7/2020 | Van Der Mee | G02B 1/11 |
| 2014/0211302 A1 | 7/2014 | Hatashita et al. | |
| 2014/0247496 A1 | 9/2014 | Kajiya et al. | |
| 2016/0161880 A1* | 6/2016 | Maeda | G03G 15/80 |
| | | | 347/118 |

FOREIGN PATENT DOCUMENTS

| | | |
|---|---|---|
| CN | 104020516 A | 9/2014 |
| CN | 107533159 A | 1/2018 |
| EP | 2653453 A1 | 10/2013 |
| JP | 2007171857 A | 7/2007 |
| JP | 2007-264613 A | 10/2007 |
| TW | 200619835 A | 6/2006 |
| WO | 2015/082948 A1 | 6/2015 |

* cited by examiner

*Primary Examiner* — Mathieu D Vargot
(74) *Attorney, Agent, or Firm* — Canon U.S.A., Inc. IP Division

(57) ABSTRACT

In a toric lens comprising a toric surface having a fine uneven structure, the fine uneven structure includes a plurality of holes, the plurality of holes have a hole depth H and a surface opening diameter φt which satisfy an expression of $0.3 \leq H/\varphi t \leq 0.6$, and (a) the plurality of holes have a hole structure having a cylindrical shape on a bottom surface side and a circular truncated cone shape having an opening diameter increasing toward a surface side, or (b) an angle θ formed between an opening portion and the surface of the plurality of holes satisfies $78° \leq \theta \leq 85°$.

13 Claims, 6 Drawing Sheets

41

TORIC LENS, OPTICAL ELEMENT, AND IMAGE FORMING APPARATUS

BACKGROUND

Field of the Disclosure

The present disclosure relates to an optical element such as a toric lens having a fine uneven structure (microstructure) on a surface thereof, and an image forming apparatus including a laser scanning optical system using the optical element.

Description of the Related Art

An optical component having a fine uneven structure with a period smaller than a wavelength of light expresses an antireflection structure, and hence there has hitherto been proposed such optical component having a fine uneven structure.

In Japanese Patent Application Laid-Open No. 2007-171857, there is disclosed an optical element having a fine uneven structure having a circular truncated cone shape on a surface. In addition, in Japanese Patent Application Laid-Open No. 2007-171857, there is also disclosed that the fine uneven structure is formed by injection molding.

However, in the optical component disclosed in Japanese Patent Application Laid-Open No. 2007-171857, in order to reduce reflectance by continuously changing a refractive index of the surface of the optical component through use of the fine uneven structure having a circular truncated cone shape, a fine uneven structure having a high aspect ratio is required. In general, in order to mold a fine uneven structure having a high aspect ratio by injection molding, molding conditions such as high temperature and high pressure are required. However, under such molding conditions, a shape deformation amount of a molded product is large, and hence there is a problem in that optical performance of the optical component is degraded.

SUMMARY

According to one aspect of the present invention, there is provided a toric lens comprising a toric surface having a fine uneven structure, wherein: the fine uneven structure includes a plurality of holes; the plurality of holes have a hole depth H and a surface opening diameter $\varphi t$ which satisfy an expression of $0.3 \leq H/\varphi t \leq 0.6$; and (a) the plurality of holes have a hole structure having a cylindrical shape on a bottom surface side and a circular truncated cone shape having an opening diameter increasing toward a surface side, or (b) an angle $\theta$ formed between an opening portion and the surface of the plurality of holes satisfies $78° \leq \theta \leq 85°$.

According to another aspect of the present invention, there is provided an optical element comprising an optical surface having a fine uneven structure, wherein: the fine uneven structure includes a plurality of holes; the plurality of holes have a hole depth H and a surface opening diameter $\varphi t$ which satisfy an expression of $0.3 \leq H/\varphi t \leq 0.6$; and (a) the plurality of holes have a hole structure having a cylindrical shape on a bottom surface side and a circular truncated cone shape having an opening diameter increasing toward a surface side, or (b) an angle $\theta$ formed between an opening portion and the surface of the plurality of holes satisfies $78° \leq \theta \leq 85°$.

According to still another aspect of the present invention, there is provided an image forming apparatus comprising: an image bearing member; a charging unit configured to charge a surface of the image bearing member; an exposing unit configured to expose the image bearing member to light using a laser optical system; and a developing unit configured to, using a developer, develop an electrostatic latent image formed on the surface of the image bearing member, wherein the laser optical system including a toric lens comprising a toric surface having a fine uneven structure, wherein: the fine uneven structure includes a plurality of holes; the plurality of holes have a hole depth H and a surface opening diameter $\varphi t$ which satisfy an expression of $0.3 \leq H/\varphi t \leq 0.6$; and (a) the plurality of holes have a hole structure having a cylindrical shape on a bottom surface side and a circular truncated cone shape having an opening diameter increasing toward a surface side, or (b) an angle $\theta$ formed between an opening portion and the surface of the plurality of holes satisfies $78° \leq \theta \leq 85°$.

Further features of the present invention will become apparent from the following description of exemplary embodiments with reference to the attached drawings.

DESCRIPTION OF THE EMBODIMENTS

A detailed description is now given of at least one embodiment of the present invention referring to drawings.

(Optical Element)

An optical element according to at least one embodiment of the present invention has a feature in that the optical element has antireflection performance due to a fine uneven structure formed on a curved surface.

Figure 1:
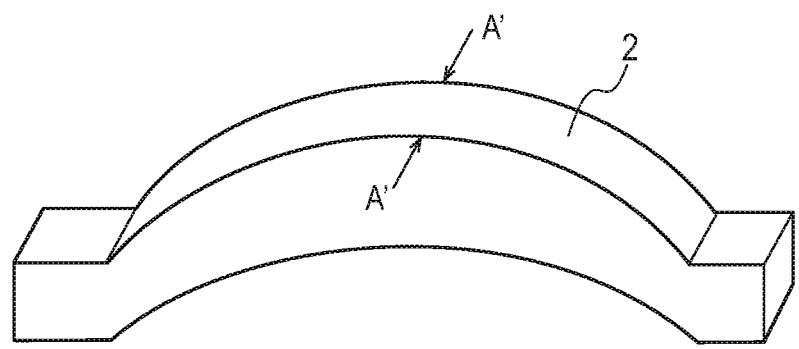
FIG. 1 is a schematic view of a toric lens according to at least one embodiment of the present invention.

As the optical element according to at least one embodiment, a mirror, a lens, a prism, or the like can be used. As the lens, a toric lens as illustrated in FIG. 1 can be used. At least one embodiment is described below through use of the toric lens.

As illustrated in FIG. 1, a toric lens 1 refers to a lens in which one surface of the lens is formed of a toric surface 2. Such toric lens is used as a component of an f-$\theta$ lens in order to correct an optical face tangle error in a laser scanning optical system. A fine uneven structure (not shown) for antireflection is formed in an effective region of the toric surface 2. It is preferred that the fine uneven structure be an injection molding formed by injection molding.

The toric lens 1 according to at least one embodiment may be formed of a single member or a plurality of members including a member having a fine uneven structure on a curved surface and another member.

As the member having a fine uneven structure and the member other than the member having a fine uneven structure, a polycarbonate resin, a polymethyl methacrylate resin, or a cycloolefin polymer resin can be used. Of those, it is preferred that the cycloolefin polymer resin having less water-absorbing property be used.

Figure 2:
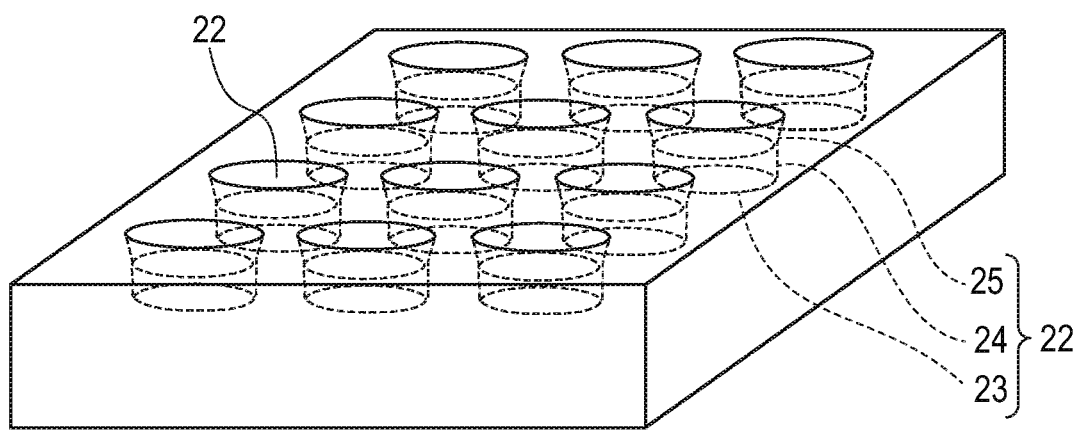
FIG. 2 is a schematic view for illustrating a fine uneven structure of an optical element according to at least one embodiment of the present invention.

FIG. 2 is an enlarged view of the toric surface 2 having the fine uneven structure of FIG. 1. In FIG. 2, the toric surface 2 is simplified and illustrated as a flat surface though the toric surface 2 is a curved surface. As illustrated in FIG. 2, the fine uneven structure is formed in an optically effective region of the toric surface 2 of the toric lens 21. The fine uneven structure is a fine uneven structure including a plurality of holes 22. Preferably but optionally, each of the holes 22 has a bottom surface 23 and a side surface extending between the bottom surface 23 and the surface 2 of the toric surface 21. A hole structure 24 proximal to the bottom surface 23 of each of the holes 22 has a cylindrical shape and a hole structure 25 distal to the bottom surface 23, that is, between the hole structure 24 and the toric surface 21 has a circular truncated cone shape with a gradually increasing diameter toward the surface 2.

Figure 3:
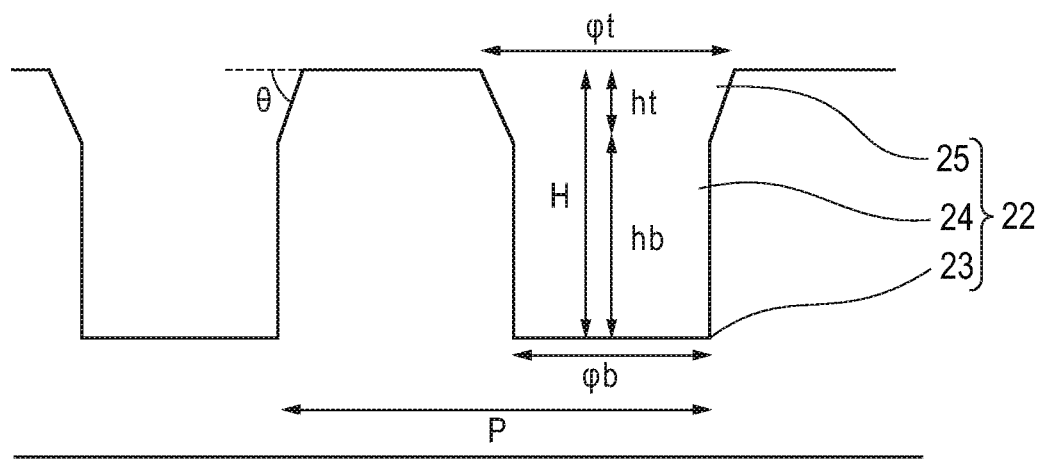
FIG. 3 is a schematic view for illustrating holes of the fine uneven structure of the optical element according to at least one embodiment of the present invention.

FIG. 3 is a sectional view of the holes 22. It is preferred that a hole depth H of the hole 22 be 80 nm or more and 185 nm or less, more preferably 100 nm or more and 165 nm or less. In addition, it is preferred that a height "nb" of the hole structure 24 having a cylindrical shape on the bottom surface 23 side be 30 nm or more and 90 nm or less, more preferably 40 nm or more and 79 nm or less. It is preferred that a height "ht" of the hole structure 25 having a circular truncated cone shape on the surface side of the hole 22 be 25 nm or more and 105 nm or less, more preferably 34 nm or more and 95 nm or less.

It is preferred that an opening diameter "$\phi t$" of the hole 22 be 150 nm or more and 450 nm or less, more preferably 198 nm or more and 407 nm or less. It is preferred that a diameter "$\phi b$" of the bottom surface 23 be 30 nm or more and 90 nm or less, more preferably 40 nm or more and 79 nm or less.

It is preferred that, in an aspect ratio ($H/\phi t$) of the hole 22, the hole depth H and the surface opening diameter "$\phi t$" satisfy an expression of $0.3 \leq H/\phi t \leq 0.6$. When $0.3 > H/\phi t$ is satisfied, antireflection performance is decreased. When $H/\phi t > 0.6$ is satisfied, a high pressure is required in injection molding, with the result that the shape accuracy of a lens surface is deteriorated.

It is preferred that an angle θ formed between an opening portion and the surface of the hole 22 satisfy an expression of $78° \leq \theta \leq 85°$. When $85° < \theta$ is satisfied, the reproducibility of a fine uneven structure dimension in injection molding is decreased. When $78° > \theta$ is satisfied, the antireflection effect is decreased.

It is preferred that the hole 22 satisfy an expression of $0.109 \leq (\phi t - \phi b)/H \leq 0.163$. When $0.109 > (\phi t - \phi b)/H$ is satisfied, the surface accuracy of the optical element is decreased. When $(\phi t - \phi b)/H > 0.163$ is satisfied, the antireflection performance is decreased.

It is preferred that an average distance interval P of the holes 22 be 100 nm or more and 1 μm or less, more preferably 250 nm or more and 500 nm or less. When the average distance interval P is less than 100 nm, the strength is decreased. When the average distance interval P is more than 1 μm, the antireflection performance is decreased. In this case, the average distance interval of the holes 22 refers to a distance between a hole and a hole located at a closest distance from the hole on the surface of the optical element. The average distance interval P is determined by averaging distances of 100 holes in a SEM image.

(Image Forming Apparatus)

Figure 4:
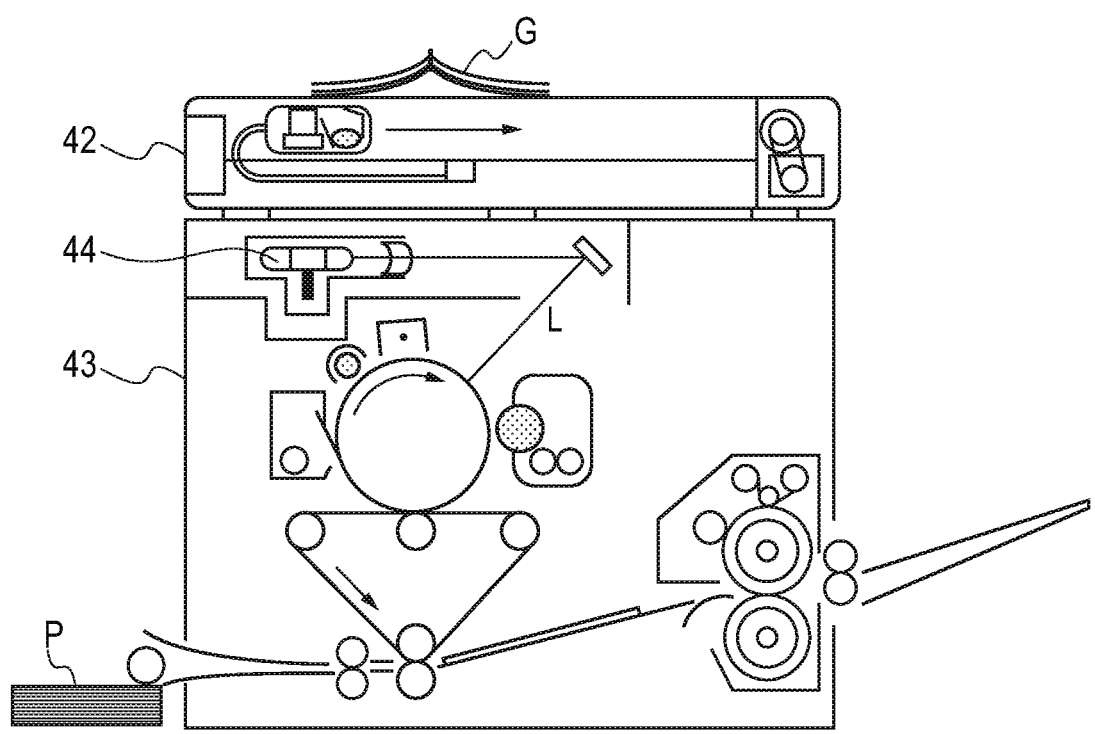
FIG. 4 is a schematic view for illustrating an image forming apparatus according to at least one embodiment of the present invention.

An image forming apparatus (electrophotographic apparatus) according to at least one embodiment of the present invention can be used in a copying machine and a multifunctional peripheral, which have a laser optical system using an optical element such as the above-mentioned toric lens. FIG. 4 is a view for illustrating a copying machine serving as the image forming apparatus. A copying machine 41 includes an image reading unit 42 and an image forming unit 43. The image forming unit 43 includes an image bearing member, a charging unit, an exposing unit, and a developing unit. The charging unit is configured to charge a surface of the image bearing member. The exposing unit is configured to expose the image bearing member to light through use of a laser optical system 44. The developing unit is configured to develop an electrostatic latent image formed on the surface of the image bearing member with a developer. The image forming unit 43 further includes a transfer unit and a fixing unit. The transfer unit is configured to transfer a developed image of the developer to a sheet. The fixing unit is configured to fix the developer transferred onto the sheet. The above-mentioned toric lens can be used in an f-θ lens of the laser optical system 44.

(Method of Manufacturing Optical Element)

Next, a method of manufacturing an optical element according to at least one embodiment of the present invention is described.

The optical element according to at least one embodiment has the fine uneven structure on an optical surface, and can be manufactured by injection molding. An injection molding piece having an uneven structure on at least one surface is prepared.

The injection molding piece can be manufactured by the following method. First, a fine uneven structure is formed on a surface of a mirror surface piece for injection molding.

Figure 5A:
FIG. 5A, FIG. 5B, FIG. 5C, and FIG. 5D are each a view for illustrating a method of manufacturing an injection molding piece in at least one embodiment of the present invention.

As illustrated in FIG. 5A, as a mirror surface piece on which a fine uneven structure is to be formed, a plating film 52 made of NiP is grown on a base material 51 made of STAVAX, and after that, the surface of the plating film 52 is smoothened.

Figure 5B:
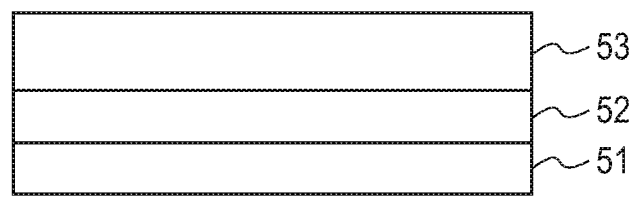

After the surface of the plating film 52 is washed, as illustrated in FIG. 5B, a $SiO_2$ film 53 is formed on the surface of the plating film 52 to a uniform thickness of 100 nm or more and 300 nm or less by sputtering. In the sputtering, the $SiO_2$ film 53 is formed by finely adjusting a ratio of an Ar gas and an $O_2$ gas through use of a Si target.

In order to control the etching depth of the $SiO_2$ film 53 with an etching selection ratio of a film composition by dry etching in a back-end process, a film rich in Si is formed in the $SiO_2$ film 53 on a side close to the plating film 52. In addition, the $SiO_2$ film having a thickness equal to or more than the depth of the hole 22 of the fine uneven structure is formed on a side away from the plating film 52.

Figure 5C:
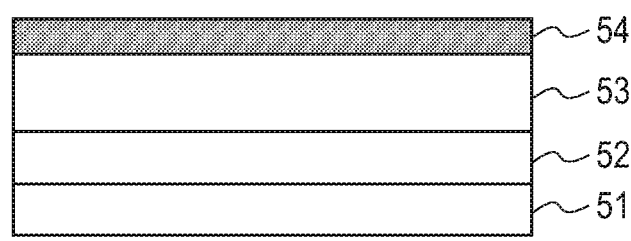

As illustrated in FIG. 5C, a photoresist 54 is applied to the surface of the $SiO_2$ film 53 to a uniform film thickness by spin coating.

Figure 5D:
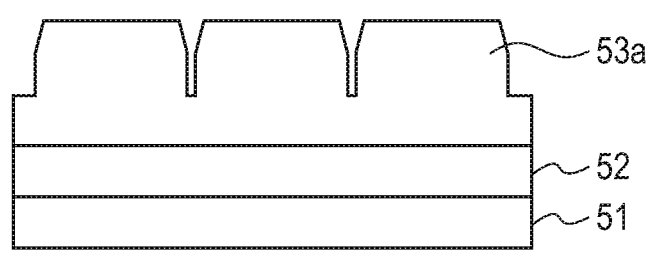

The resultant is subjected to drying treatment such as prebaking. Then, as illustrated in FIG. 5D, patterns each having a substantially cylindrical shape are drawn in a direction perpendicular to a curved surface of the mirror surface piece by electron beam drawing.

Fine uneven structure patterns, each having, in the substantially cylindrical shape, a cylindrical shape in a lower stage and a circular truncated cone shape having a hole diameter decreasing toward the surface in an upper stage, are formed at an average pitch interval of 100 nm or more and 1 µm or less, preferably 250 nm or more and 500 nm or less.

In injection molding, a molten resin is filled between the fine uneven structure patterns at a high pressure of 40 MPa or more, and hence the resin is swollen through stress relaxation after molding release. It is required that the size of each of the fine uneven structure patterns be corrected for shape in consideration of stress relaxation as compared to a hole diameter in size to be finally obtained in a molded product.

Although it also relates to injection molding conditions and the like, the cylindrical shape in the lower stage of each of the fine uneven structure patterns formed on the piece surface is drawn so that the diameter thereof becomes thicker by a little more than 20 nm because gaps between the respective adjacent patterns become narrower and swelling is strengthened in molding release, and the circular truncated cone shape in the upper stage of each of the fine uneven structure patterns is drawn so that the diameter thereof becomes thicker by a little less than 10 nm because gaps between the respective adjacent patterns are enlarged and the swelling is weakened in molding release.

The thickness of the photoresist 54 used in a drawing step is related to the fine uneven structure formed on the surface of the mirror surface piece. Specifically, when the height of the fine uneven structure is set to 120 nm, the thickness of the photoresist 54 of 90 nm or more is required based on the selection ratio in dry etching.

Regarding the photoresist 54, interface reflection is appropriately reduced by treatment of bark and talc in accordance with the specifications of a drawing device or the like.

Drawing patterns are formed by immersing the mirror surface piece after drawing in a developing solution. After that, the resultant is subjected to postbaking treatment. With this, similar patterns in which the fine uneven structure to be formed by dry etching is reduced in a height direction are formed on the $SiO_2$ film. The $SiO_2$ film is etched by a thickness of 120 nm by dry etching using a $CHF_3$ gas with the photoresist 54 being a mask, to thereby uniformly form the fine uneven structure with a period equal to or less than a wavelength of preventing reflection on the surface of the mirror surface piece. Ashing treatment is performed with an oxygen gas after dry etching to remove a residue of the photoresist 54, and thus a mirror surface piece for injection molding including a $SiO_2$ film 53a having a fine uneven structure formed thereon is manufactured.

A fine uneven structure is uniformly formed also on the surface of the injection molding piece on an opposite side in a similar manner.

A method of forming a fine uneven structure with a period equal to or less than a wavelength of preventing reflection on the surface of the mirror surface piece for injection molding is not limited to the method described above.

Figure 6A:
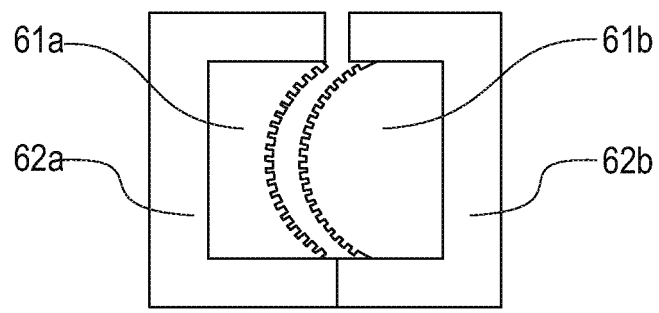
FIG. 6A, FIG. 6B, and FIG. 6C are each a view for illustrating a method of manufacturing an optical element according to at least one embodiment of the present invention.

Next, as illustrated in FIG. 6A, pieces 61a and 61b each having fine uneven structure patterns formed on the surface of the mirror surface piece are incorporated into a fixed-side mold 62a and a movable-side mold 62b of an injection molding device, respectively, and an optical element having a fine uneven structure configured to exhibit an antireflection function is formed by injection molding.

Figure 6B:
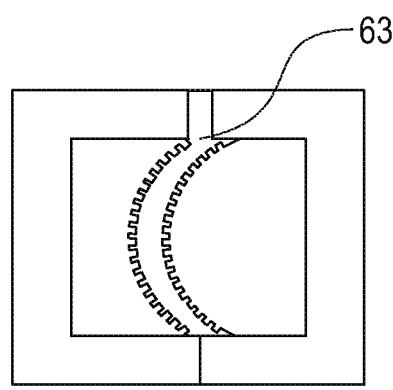

As illustrated in FIG. 6B, an uncured resin 63 is molded through a resin injection step of injecting the uncured resin 63 into between a set of pieces. As the resin for injection molding, a thermoplastic resin such as a cycloolefin polymer resin having less water-absorbing property, a polycarbonate resin, or a polymethyl methacrylate resin can be used. Of those, it is preferred that the cycloolefin polymer resin having less water-absorbing property be used. When the cycloolefin polymer resin is used, it is preferred that the molten resin temperature be 250° C. or more and 290° C. or less, the mold temperature be 125° C. or more and 140° C. or less, and the holding pressure be 20 MPa or more and 90 MPa or less.

Figure 6C:
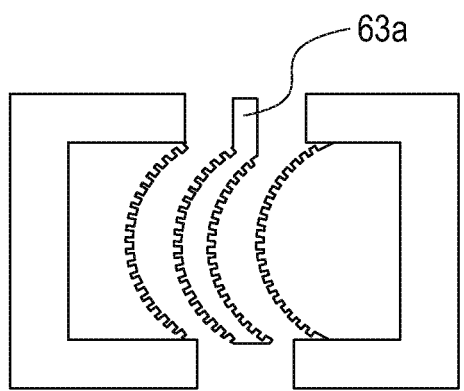

As illustrated in FIG. 6C, after the molded resin temperature is cooled to a temperature equal to or less than a glass transition temperature, a molded product is released so as not to be inclined through use of an ejector pin, to thereby obtain an optical element 63a.

The fine uneven structure on the piece surface has a two-stage structure in which the circular truncated cone shape having an upper hole diameter decreasing is laminated on the cylindrical shape. However, such fine shape is not directly transferred onto the molded optical element obtained by injection molding. A hole structure having a cylindrical shape is formed on a substrate side, and a hole structure having a circular truncated cone shape with an opening diameter increasing toward a surface side is formed.

The molten resin is filled into between the set of pieces, followed by transfer at a high pressure. Therefore, stress relaxation occurs after molding, and a cylindrical hole having a substantially perpendicular shape is formed in a part having the circular truncated cone shape of the piece. In addition, a circular truncated cone shape having an opening diameter increasing toward the surface is formed in a part having the cylindrical shape of the piece due to stress relaxation. In stress relaxation, the cylindrical hole diameter is narrowed by about a little less than 10 nm on the substrate side of the molded product, and the opening diameter of the circular truncated cone hole on the surface side is narrowed by about a little less than 20 nm. Therefore, an antireflection optical member, in which a shape correction amount of the fine uneven structure formed on the piece is reflected, is obtained. In the molded optical member obtained by injection molding under a condition of a piece structure having a stress relaxation amount controlled, a two-stage structure is formed. In the two-stage structure, a hole structure having a cylindrical shape configured to decrease reflectance is formed on the substrate side, and a side wall inclined portion contributing to reflection is decreased accordingly.

The optical element having the fine uneven structure on the surface of the present invention is excellent in antireflection performance, and a manufacturing cost can be reduced.

In the method of manufacturing an optical element such as the toric lens of the present invention, a fine uneven structure is formed by injection molding. Therefore, the manufacturing time can be shortened, and the manufacturing cost can be reduced.

EXAMPLES

In the following Examples and Comparative Examples, manufactured optical elements were evaluated by the following methods.

(Measurement of Reflectance)

Reflectance was measured through use of a microscopic spectroscopic device (USPM-RUII manufactured by Olympus Corporation). The measurement conditions were an objective lens magnification of 10 times, and a measurement wavelength of from 380 nm to 780 nm. In addition, in the obtained reflection spectral characteristics, a local minimum value of reflectance was represented by Rmin.

Example 1

First, an injection molding piece was manufactured by the following method.

As illustrated in FIG. 5A, a set of mirror surface pieces, on each of which a fine uneven structure was to be formed, were manufactured. The set of mirror surface pieces had a concave shape and a convex shape, respectively, and each had a dimension of 20 nm in a longitudinal direction and a dimension of 5 nm in a short direction. The plating film 52 made of NiP was grown on the base material 51 made of STAVAX, and after that, the surface of the plating film 52 was subjected to mirror finishing so that the thickness of the plating film 52 of about 30 μm was left in accordance with a lens surface.

Next, as illustrated in FIG. 5B, after the mirror surface of NiP was washed, the $SiO_2$ film 53 was formed on the NiP surface to a uniform thickness of 200 nm by sputtering. In the $SiO_2$ film 53, first, a film rich in Si was formed on the NiP surface, and then the $SiO_2$ film was formed in the thickness corresponding to the depth of the fine uneven structure.

As illustrated in FIG. 5C, the photoresist 54 was applied to the surface of the $SiO_2$ film 53 to a uniform film thickness by spin coating.

After drying treatment, as illustrated in FIG. 5D, patterns each having a substantially cylindrical shape were drawn in a direction perpendicular to a curved surface of the mirror surface piece by electron beam drawing. Fine uneven structure patterns, each having, in the substantially cylindrical shape, a cylindrical shape in a lower stage and a circular truncated cone shape having a hole diameter decreasing toward a surface in an upper stage, were formed at an average pitch interval of 250 nm. In Example 1, in the substantially cylindrical shape, the lower stage was formed into a cylindrical shape having a diameter of about 228 nm and a height of about 54 nm. In addition, the upper stage was formed into a circular truncated cone shape having a height of about 56 nm with a taper angle of about 79 degrees.

As illustrated in FIG. 6A, a set of molding pieces thus manufactured, each having the fine uneven structure patterns formed on the surface of the mirror surface piece, were incorporated into a fixed side and a movable side of the injection molding device, respectively, and an optical element having a fine uneven structure with a period equal to or less than a wavelength of exhibiting an antireflection function was formed by injection molding.

As illustrated in FIG. 6B, an uncured cycloolefin resin was injected into between the set of molding pieces and molded. It is preferred that the cycloolefin resin be molded at a molten resin temperature of 270° C., a mold temperature of 140° C. or less, and a holding pressure of from 20 MPa or more and 90 MPa or less. In addition, the molding was performed at an injection molding speed of 30 mm/sec.

As illustrated in FIG. 6C, the resultant was cooled and released from the molds to obtain an optical element. The fine uneven structure on the surface of the optical element had a shape as shown in Table 1.

In the hole structure having a two-stage structure in Example 1, the depth of the hole structure having a substantially circular truncated cone shape with an inclined side surface can be set to be as small as 54 nm though the aspect ratio is as low as 0.53. Therefore, there is an effect of suppressing an increase in reflectance with respect to a set wavelength in ordinary injection molding.

Comparative Example 1

In Comparative Example 1, an optical element, in which a side wall of a fine hole structure was formed substantially perpendicularly, was manufactured in the same manner as in Example 1 except that the cylindrical shape formed on the molding piece was changed, and that the injection molding speed was set to be extremely low to about 2 mm/sec to perform molding.

Each dimension and characteristics of the fine uneven structure of the optical element are shown in Table 1.

In the optical element of Comparative Example 1, the molded resin did not sufficiently reach a side opposite to an injection gate due to the low injection molding speed, and the fine uneven structure on the side opposite to the injection gate was formed to be smaller than a desired height, with the result that reflectance was significantly increased. Specifically, the height of the fine uneven structure on the side opposite to the injection gate was about 40 nm, and reflectance was about 1%.

Example 2

In Example 2, an optical element, in which a side wall of a fine hole structure was formed substantially perpendicularly, was manufactured in the same manner as in Example 1 except that the cylindrical shape formed on the molding piece was changed. In Example 2, the cylindrical shape was formed in portions on the molding piece at pitch intervals of 250 nm. In the substantially cylindrical shape, the lower stage was formed into a cylindrical shape having a diameter of about 218 nm and a height of about 41 nm. In addition, the upper stage was formed into a circular truncated cone shape having a height of about 79 nm with a taper angle of about 81 degrees.

Each dimension and characteristics of the fine uneven structure of the optical element are shown in Table 1.

Example 3

In Example 3, an optical element, in which a side wall of a fine hole structure was formed substantially perpendicularly, was manufactured in the same manner as in Example 1 except that the cylindrical shape formed on the molding piece was changed. In Example 3, the cylindrical shape was formed in portions on the molding piece at pitch intervals of about 250 nm. In the substantially cylindrical shape, the lower stage was formed into a cylindrical shape having a diameter of about 218 nm and a height of about 34 nm. In addition, the upper stage was formed into a circular truncated cone shape having a height of about 66 nm with a taper angle of about 79 degrees.

Each dimension and characteristics of the fine uneven structure of the optical element are shown in Table 1.

Example 4

In Example 4, an optical element, in which a side wall of a fine hole structure was formed substantially perpendicularly, was manufactured in the same manner as in Example 1 except that the cylindrical shape formed on the molding piece was changed. In Example 4, the cylindrical shape was formed in portions on the molding piece at pitch intervals of about 250 nm. In the cylindrical shape, the lower stage was formed into a cylindrical shape having a diameter of about 228 nm and a height of about 70 nm. In addition, the upper stage was formed into a circular truncated cone shape having a height of about 40 nm with a taper angle of about 75 degrees.

Each dimension and characteristics of the fine uneven structure of the optical element are shown in Table 1.

Example 5

In Example 5, an optical element, in which a side wall of a fine hole structure was formed substantially perpendicularly, was manufactured in the same manner as in Example 1 except that the cylindrical shape formed on the molding piece was changed. In Example 5, the cylindrical shape was formed in portions on the molding piece at pitch intervals of about 500 nm. In the cylindrical shape, the lower stage was formed into a cylindrical shape having a diameter of about 427 nm and a height of about 95 nm. In addition, the upper stage was formed into a circular truncated cone shape having a height of about 70 nm with a taper angle of about 75 degrees.

Each dimension and characteristics of the fine uneven structure of the optical element are shown in Table 1.

Comparative Example 2

In Comparative Example 2, an optical element, in which a side wall of a fine hole structure was formed substantially perpendicularly, was manufactured in the same manner as in Example 1 except that the cylindrical shape formed on the molding piece was changed, and that the injection molding speed was set to 30 mm/sec to perform molding. In the optical element of Comparative Example 2, the molded resin was not sufficiently filled into the fine uneven structure of the piece. Therefore, the reflection characteristics of molded products were varied due to slight variation in injection molding conditions, and reproducibility was decreased. Specifically, the value of 3σ was about 0.05, and molded products having a reflectance of about 0.1% were also included.

Each dimension and characteristics of the fine uneven structure of the optical element are shown in Table 1.

or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2018-195286, filed Oct. 16, 2018, which is hereby incorporated by reference herein in its entirety.

TABLE 1

| Dimension of fine uneven structure | Example 1 | Example 2 | Example 3 | Example 4 | Example 5 | Comparative Example 1 | Comparative Example 2 |
|---|---|---|---|---|---|---|---|
| P (nm) | 250 | 250 | 250 | 250 | 500 | 250 | 250 |
| Φt (nm) | 208 | 198 | 198 | 208 | 407 | 196 | 211 |
| Φb (nm) | 196 | 183 | 183 | 196 | 380 | 196 | 196 |
| H (nm) | 110 | 120 | 100 | 110 | 165 | 110 | 110 |
| ht (nm) | 54 | 41 | 34 | 70 | 95 | 0 | 110 |
| hb (nm) | 56 | 79 | 66 | 40 | 70 | 0 | 0 |
| θ (degee) | 82 | 80 | 78 | 85 | 82 | 90 | 86 |
| Aspect ratio | 0.5 | 0.6 | 0.5 | 0.5 | 0.4 | 0.6 | 0.5 |
| Rmin (%) | 0.01 | 0.05 | 0.08 | 0.01 | 0.03 | 0.03 | 0.05 |

(Evaluation)

In the hole structure having the two-stage structure in Example 1, the depth of the hole structure having a substantially circular truncated cone shape with an inclined side surface can be set to be as small as 54 nm although the aspect ratio is as low as 0.53. Therefore, there is an effect of suppressing an increase in reflectance with respect to a set wavelength in ordinary injection molding.

OTHER EMBODIMENTS

Embodiment(s) of the present invention can also be realized by a computer of a system or apparatus that reads out and executes computer executable instructions (e.g., one

What is claimed is:

1. An optical element comprising an optical surface having a plurality of holes, wherein
the plurality of holes has a hole depth H and a surface opening diameter φt which satisfy an expression of $0.3 \leq H/\varphi t \leq 0.6$, and
the plurality of holes has a circular truncated cone shape distal to a bottom surface and proximal to a top surface of the optical surface, the circularly truncated cone shape having a diameter gradually increasing toward the top surface of the optical surface, and
the circular truncated cone shape has a height ht which satisfies an expression of $0.34 \leq ht/H \leq 0.64$.

2. The optical element according to claim 1, wherein the optical surface has a fine uneven structure including the plurality of holes, the fine uneven structure is formed by injection molding.

3. The optical element according to claim 1, wherein the optical surface has a fine uneven structure, the fine uneven structure is made of a cycloolefin polymer resin.

4. The optical element according to claim 1, wherein the optical element is formed of a single member.

5. An image forming apparatus, comprising:
an image bearing member;
a charging unit configured to charge a surface of the image bearing member;
a laser optical system member;
an exposing unit configured to expose the image bearing member to light using the laser optical system; and
a developing unit configured to, using a developer, develop an electrostatic latent image formed on the surface of the image bearing member, wherein
the laser optical system member including an optical element comprising an optical surface having a plurality of holes, the plurality of holes has a hole depth H and a surface opening diameter φt which satisfy an expression of $0.3 \leq H/\varphi t \leq 0.6$, and
the plurality of holes has a a circular truncated cone shape having a diameter gradually increasing toward the top surface of the optical surface, and
the circular truncated cone shape has a height ht satisfies an expression of $0.34 \leq ht/H \leq 0.64$.

6. The optical element according to claim 1, wherein a distance between two closest holes is no smaller than about 100 nm or no larger than about 1 μm.

7. The optical element according to claim 1, wherein an angle θ between the top surface and a side surface of the circular truncated cone shape of the plurality of holes satisfies $78° \leq \theta \leq 85°$.

8. The optical element according to claim 1, wherein the plurality of holes has a cylindrical shape proximal to the bottom surface.

9. The optical element according to claim 1, wherein the optical surface has a fine uneven structure including the plurality of holes, the fine uneven structure is made of resin.

10. The optical element according to claim 1, wherein the surface opening diameter φt of the holes is no less than 150 nm and no larger than about 450 nm.

11. The optical element according to claim 1, wherein the optical element is a toric lens and the optical surface is a toric surface.

12. The optical element according to claim 11, wherein the optical element is lighted using a laser optical system.

13. The optical element according to claim 11, wherein a wavelength of a light through use of an element lighting laser optical system is from 380 nm to 780 nm, and a distance between two neighboring holes is no less than 250 nm and no larger than 500 nm.

* * * * *